United States Patent
Sugimura et al.

(10) Patent No.: US 6,344,046 B2
(45) Date of Patent: Feb. 5, 2002

(54) CORNEAL SURGICAL APPARATUS

(75) Inventors: Masahiro Sugimura; Ryoji Shibata, both of Aichi (JP)

(73) Assignee: Nidek Co., Ltd, Gamagori (JP)

(*) Notice: Subject to any disclaimer, the term of this patent is extended or adjusted under 35 U.S.C. 154(b) by 0 days.

(21) Appl. No.: 09/753,568

(22) Filed: Jan. 4, 2001

Related U.S. Application Data

(62) Division of application No. 09/517,188, filed on Mar. 2, 2000, now Pat. No. 6,203,555.

(30) Foreign Application Priority Data

Mar. 3, 1999 (JP) .............................................. 11-55696
Mar. 31, 1999 (JP) .............................................. 11-90337

(51) Int. Cl.$^7$ ................................................. A61F 9/00
(52) U.S. Cl. ..................................................... 606/166
(58) Field of Search ................................ 606/166, 167, 606/107, 161, 108, 169, 172

(56) References Cited

U.S. PATENT DOCUMENTS

| | | | |
|---|---|---|---|
| 4,662,370 A | 5/1987 | Hoffman et al. | |
| 4,903,695 A | 2/1990 | Warner et al. | |
| RE35,421 E | 1/1997 | Ruiz et al. | |
| 5,595,570 A | 1/1997 | Smith | |
| 5,624,456 A | 4/1997 | Hellenkamp | |
| 5,779,723 A | 7/1998 | Schwind | |
| 5,964,776 A | * 10/1999 | Peyman | ...................... 606/166 |
| 5,972,011 A | * 10/1999 | Peirce et al. | ................. 606/166 |
| 6,045,562 A | 4/2000 | Amano et al. | |
| 6,059,805 A | 5/2000 | Sugimura et al. | |

FOREIGN PATENT DOCUMENTS

| | | |
|---|---|---|
| EP | 0956840 | 11/1999 |
| JP | A 11-99167 | 4/1999 |

* cited by examiner

*Primary Examiner*—Kevin Truong
(74) *Attorney, Agent, or Firm*—Finnegan, Henderson, Farabow, Garrett & Dunner, L.L.P.

(57) ABSTRACT

A corneal surgical apparatus for incising a cornea of a patient's eye in a layered form includes: a suction ring unit, having a circular opening, that is to be vacuum-fixed onto a peripheral part of the cornea; a rotatable shaft; an eccentric pin projecting from a distal end of the shaft, the eccentric pin being located at a position offset from a rotational central axis of the shaft; and a cutting unit movable in an incising direction above the suction ring unit. The cutting unit including: cornea applanating means that applanates the cornea within the opening into a substantially flat form; a blade that incises the cornea; a first oscillation transmitting member having a part with which the eccentric pin is engaged; a second oscillation transmitting member having a part with which a part of the first oscillation transmitting member is engaged; and a holder that holds the first and second oscillation transmitting members to be movable in a lateral direction which is perpendicular to the rotational central axis of the shaft. Movement of the second oscillation transmitting member in the lateral direction causes the blade to be moved in the same direction.

12 Claims, 10 Drawing Sheets enlarged cross-sectional view taken on the line A-A enlarged cross-sectional view taken on the line B-B

- 33 pressure detector
- 40 control unit
- 41 pump
- 42 foot switch enlarged cross-sectional view taken on the line C-C cornea applanating member suction ring rotation center

CORNEAL SURGICAL APPARATUS

This is a division of application Ser. No. 09/517,188, filed Mar. 2, 2000 now U.S. Pat. No. 6,203,555, which is incorporated herein by reference.

BACKGROUND OF THE INVENTION

1. Field of the Invention

The present invention relates to a corneal surgical apparatus for incising the cornea of an eye of a patient in a layered form at the time of a keratorefrative surgery or the like.

2. Description of the Related Art

In recent years, attention has been focused on a LASIK surgery (laser in situ keratomileusis) for the keratorefractive surgery wherein a flap is formed by incising a portion with a thickness of about 0.15 mm from the corneal epithelium to the corneal stroma with a part of the cornea remaining connected like a hinge, ablating the corneal stroma in a refractive correction amount by an excimer laser light, and returning the flap to its original position. In the LASIK surgery, a corneal surgical apparatus called microkeratome is used for incising the cornea in a layered form.

As a corneal surgical apparatus, one comprising a suction ring to be vacuum-fixed to a part of the cornea from a corneal ring portion to the surface of the conjunctiva, a cornea applanating member for applanating the cornea flatly, and a blade movable toward the hinge while being oscillated laterally so as to incise the flattened cornea into a layer form with a substantially uniform thickness, is known.

As a mechanism for the blade lateral oscillation, as shown in FIG. 13A, one comprising a rotation shaft 301 to be rotated by a driving device such as a motor, an eccentric pin 302 provided at the tip end of the shaft 301, a transmitting member 304 having a vertical groove 303 to be engaged with the pin 302 is proposed. The transmitting member 304 having a blade 300 fixed thereto is held movably in the lateral direction (right and left direction, that is, the direction perpendicular to the paper surface in FIG. 13) in a receiving groove formed in a blade holder 305 and a holder block 306. When the shaft 301 is rotated by drive of the motor, force is applied on the transmitting member 304 in the lateral direction according to the circumferential movement (circular motion) of the pin 302 engaged with the vertical groove 303. Accordingly, the transmitting member 304 oscillated laterally (moved in the right and left direction), and further, the blade 300 fixed to the transmitting member 304 is oscillated laterally as well.

However, according to the conventional mechanism, as shown in FIG. 13B, by the circumferential movement of the pin 302, not only the force in the lateral direction but also force in the vertical direction (up and down direction) is applied to the transmitting member 304. That is, since the pin 302 with the circumferential movement comes in contact with the wall of the vertical groove 303 so that force is applied on the transmitting member 304 in the vertical direction due to the friction force generated by the contact, the transmitting member 304 is oscillated laterally while being moved-also in the vertical direction. Therefore, if the shaft 301 is rotated at a high speed, the transmitting member 304 and the blade 300 generate vertical oscillation (up and down movement) called "rampage" in addition to the lateral oscillation.

The "rampage" hinders stable incision as well as generates a loss in terms of the efficiency of converting the rotational motion to the lateral oscillation. Moreover, since the corner part of the transmitting member 304 is contacted with a blade holder 305 and the holder block 306 frequently so as to be applied with a large force, the parts are worn out rapidly so that the life cycle thereof is shortened.

The displacement amount of the transmitting member 304 to be displaced vertically and laterally (in the up and down, and right and left directions) according to the circumferential movement of the pin 302 corresponds to the eccentric amount of the pin 302, but as to the vertical direction, since the transmitting member 304 is held by the blade holder 305 and the holder block 306 in the vertical direction, the transmitting member 304 (and the blade 300) is displaced (vertical oscillation) for the gap with respect to each member. Therefore, accurate production without a gap among the transmitting member 304, the blade holder 305 and the holder block 306 would prevent the vertical oscillation (that is, "rampage"), however, much labor is required for meeting the demand particularly in mass production so as to increase the cost.

SUMMARY OF THE INVENTION

In view of the above-mentioned problems, an object of the present invention is to provide a corneal surgical apparatus capable of forming a good flap by preventing "rampage" of a blade. Effects of the apparatus include efficient generation of lateral oscillation, restraint of the cost rise according to high accuracy of the mechanism, and high durability.

In order to solve the above-mentioned problems, the invention is characterized by the following features.

(1) A corneal surgical apparatus for incising a cornea of a patient's eye in a layered form, comprising:
  a suction ring unit, having a circular opening, that is to be vacuum-fixed onto a peripheral part of the cornea;
  a rotatable shaft;
  an eccentric pin projecting from a distal end of the shaft, the eccentric pin being located at a position offset from a rotational central axis of the shaft; and
  a cutting unit movable in an incising direction above the suction ring unit, the cutting unit including:
    cornea applanating means that applanates the cornea within the opening into a substantially flat form;
    a blade that incises the cornea;
    a first oscillation transmitting member having a part with which the eccentric pin is engaged;
    a second oscillation transmitting member having a part with which a part of the first oscillation transmitting member is engaged; and
    a holder that holds the first and second oscillation transmitting members to be movable in a lateral direction which is perpendicular to the rotational central axis of the shaft,
  wherein movement of the second oscillation transmitting member in the lateral direction causes the blade to be moved in the same direction.

(2) A corneal surgical apparatus according to (1), wherein the blade is fixed to the second oscillation transmitting member.

(3) A corneal surgical apparatus according to (1), wherein the first oscillation transmitting member includes:
  a vertical groove elongating in a direction perpendicular to both of the lateral direction and the rotational central axis of the shaft, the eccentric pin being engaged with the vertical groove; and
  a pin part extending toward the second oscillation transmitting member;

wherein the second oscillation transmitting member includes a pin receiving part with which the pin part of the first oscillation transmitting member is engaged.

(4) A corneal surgical apparatus according to (1), wherein the holder holds the first and second oscillation transmitting member to be movable linearly in the lateral direction.

(5) A corneal surgical apparatus according to (1), wherein the first oscillation transmitting member includes a shaft part rotatable about an axis different in location from the rotational central axis of the shaft, the shaft part having at least one of a recess and a protrusion, and wherein the holder includes a bearing part that rotatably supports the shaft part and that has a part with which the shaft part is engaged, the holder holding the first oscillation transmitting member to be rockable in the lateral direction.

(6) A corneal surgical apparatus according to (5), wherein the holder holds the second oscillation transmitting member to be movable linearly in the lateral direction.

(7) A corneal surgical apparatus according to (5), wherein the shaft part of the first oscillation transmitting member includes two shaft parts respectively located on an upper part and a lower part of the first oscillation transmitting member, and wherein the bearing part includes two bearing parts respectively supporting the two shaft parts.

(8) A corneal surgical apparatus according to (5), wherein the shaft part of the first oscillation transmitting member is rotatable about an axis intersecting the rotational central axis of the shaft.

(9) A corneal surgical apparatus according to (8), wherein the rotational central axis of the shaft part of the first oscillation transmitting member intersects the rotational central axis of the shaft perpendicularly.

(10) A corneal surgical apparatus according to (9), wherein the eccentric pin is provided on an axis passing through an intersecting point at which the rotational central axis of the shaft part intersects the rotational central axis of the shaft.

(11) A corneal surgical apparatus according to (1), wherein the eccentric pin is provided on an axis non-perpendicularly intersecting the rotational central axis of the shaft.

(12) A corneal surgical apparatus according to (1), further comprising:
a drive unit that rotates the shaft.

(13) A corneal surgical apparatus according to (1), further comprising:
a drive unit that moves the cutting unit in the incising direction.

(14) A corneal surgical apparatus for incising a cornea of a patient's eye in a layered form, comprising:
a suction ring unit, having a circular opening, that is to be vacuum-fixed onto a peripheral part of the cornea;
a rotatable shaft;
an eccentric pin projecting from a distal end of the shaft, the eccentric pin being located at a position offset from a rotational central axis of the shaft; and
a cutting unit movable in an incising direction above the suction ring unit, the cutting unit including:
cornea applanating means that applanates the cornea within the opening into a substantially flat form;
a blade that incises the cornea;
a rock transmitting member having a part with which the eccentric pin is engaged and a shaft part rotatable about an axis different in location from the rotational central axis of the shaft, the shaft part having at least one of a recess and a protrusion; and
a holder that holds the rock transmitting members to be rockable in a lateral direction which is perpendicular to the rotational central axis of the shaft, the holder having a bearing part rotatably supporting the shaft part of the rock transmitting member, the bearing part having a part with which the shaft part is engaged,
wherein movement of the rock transmitting member in the lateral direction causes the blade to be moved in the same direction.

(15) A corneal surgical apparatus according to (14), wherein the shaft part of the rock transmitting member includes two shaft parts respectively located on an upper part and a lower part of the rock transmitting member, and
wherein the bearing part includes two bearing parts respectively supporting the two shaft parts.

(16) A corneal surgical apparatus according to (14), wherein the shaft part of the rock transmitting member is rotatable about an axis intersecting the rotational central axis of the shaft.

(17) A corneal surgical apparatus according to (16), wherein the rotational central axis of the shaft part of the rock transmitting member perpendicularly intersects the rotational central axis of the shaft.

(18) A corneal surgical apparatus according to (17), wherein the eccentric pin is provided on an axis passing through an intersecting point at which the rotational central axis of the shaft part intersects the rotational central axis of the shaft.

(19) A corneal surgical apparatus according to (14), wherein the eccentric pin is provided on an axis which non-perpendicularly intersects the rotational central axis of the shaft.

(20) A corneal surgical apparatus according-to (14), further comprising:
a drive unit that rotates the shaft.

(21) A corneal surgical apparatus according to (14), further comprising:
a drive unit that moves the cutting unit in the incising direction.

(22) A corneal surgical apparatus for incising a cornea of a patient's eye in a layered form, comprising:
a suction ring unit, having a circular opening, that is to be vacuum-fixed onto a peripheral part of the cornea;
a rotatable shaft;
an eccentric pin projecting from a distal end of the shaft, the eccentric pin being provided on an axis non-parallel to and non-perpendicular to a rotational central axis of the shaft; and
a cutting unit movable in an incising direction above the suction ring unit, the cutting unit including:
cornea applanating means that applanates the cornea within the opening into a substantially flat form;
a blade that incises the cornea;
a transmitting member having a part with which the eccentric pin is engaged; and
a holder that holds the transmitting member to be movable in a lateral direction which is perpendicular to the rotational central axis of the shaft,
wherein movement of the transmitting member in the lateral direction causes the blade to be moved in the same direction.

(23) A corneal surgical apparatus according to (22), wherein the eccentric pin is provided on an axis that non-perpendicularly intersects the rotational central axis of the shaft.

(24) A corneal surgical apparatus according to (22), further comprising:

a drive unit that rotates the shaft.

(25) A corneal surgical apparatus according to (22), further comprising:

a drive unit that moves the cutting unit in the incising direction.

The present disclosure relates to the subject matter contained in Japanese patent application Nos. Hei. 11-55696 (filed on Mar. 3, 1999) and Hei. 11-90337 (filed on Mar. 31, 1999), which are expressly incorporated herein by reference in their entireties.

DETAILED DESCRIPTION OF THE PREFERRED EMBODIMENTS

First Embodiment

Figure 1:
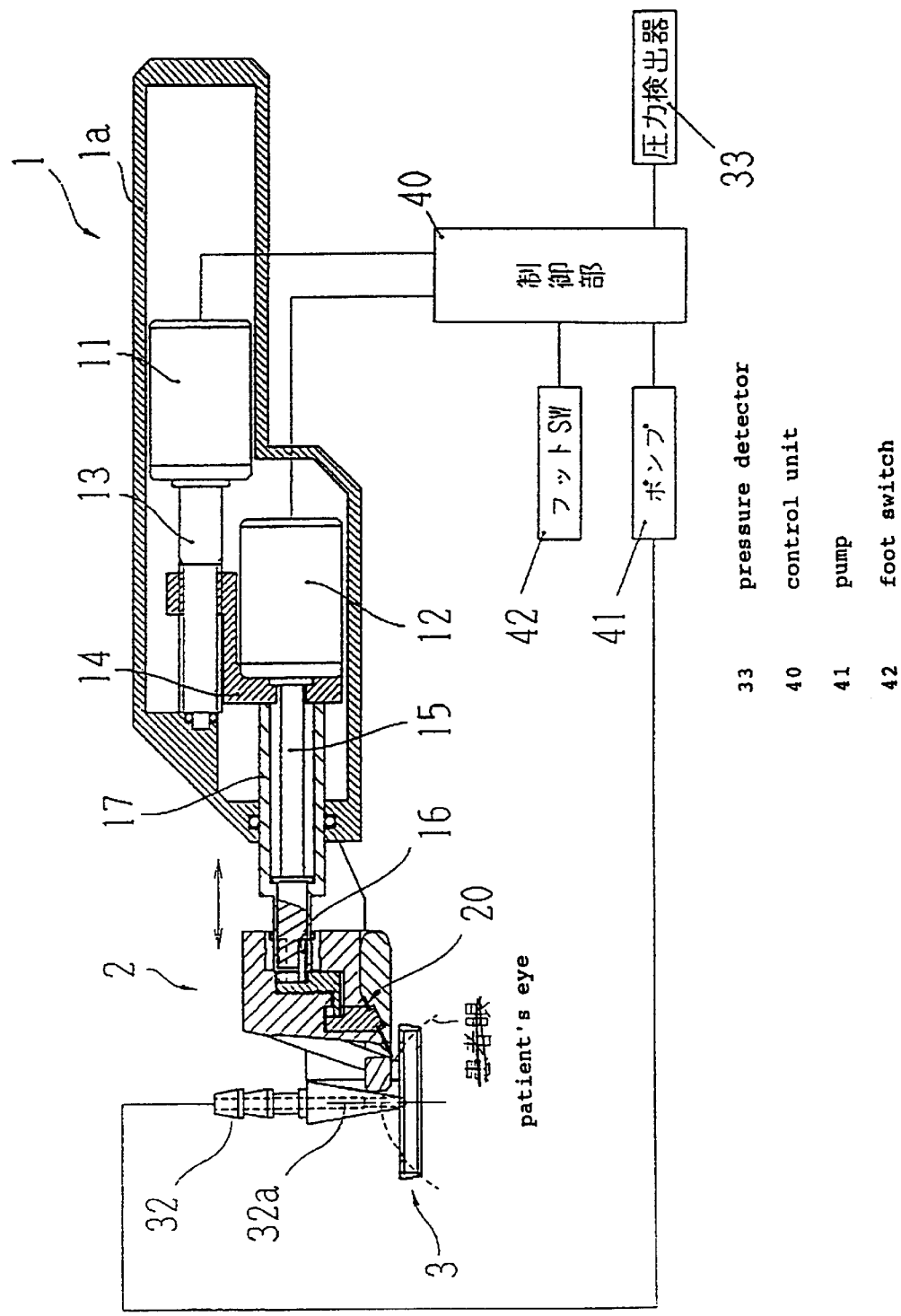
FIG. 1 is a cross-sectional view of an apparatus according to a first embodiment and a schematic diagram of a control system.

Hereinafter an embodiment of the invention will be explained with reference to the drawings. FIG. 1 is a cross-sectional view of a corneal surgical apparatus according to a first embodiment and a schematic diagram of a control system.

Reference numeral 1 denotes a main body of the apparatus, and numeral 1a denotes a grip portion to be held by an operator during a surgery. A suction unit 3 for fixation to the patient's eye, and a cutting unit 2 having a blade 20 for incising the cornea, to be moved rectilinearly above the suction unit 3 are provided on the front side (left side in the figure) of the main body 1.

A feed motor 11 for rectilinearly moving the-cutting unit 2 in the incising direction is fixed in the main body 1, with a feed screw 13 having a threaded portion corresponding in length to the rectilinear movement of the cutting unit 2, attached to the rotation shaft of the motor 11. An oscillating motor 12 for imparting lateral oscillation to the blade, and a connecting member 17 to be connected with the cutting unit 2 at its tip portion are fixed to an attaching member 14 to be screwed into the threaded portion of the screw 13. A rotation shaft 15 mounted on the rotation shaft of the motor 12 is held by the connecting member 17 rotatably. An eccentric pin 16 is embedded on the tip of the shaft 15 at a position offset from the rotation center (rotation central axis), projecting therefrom. The cutting unit 2 moves forward or backward with the motor 12 and the connecting member 17 mounted on the attaching member 14 according to the forward or reverse rotation of the motor 11.

Figure 2:
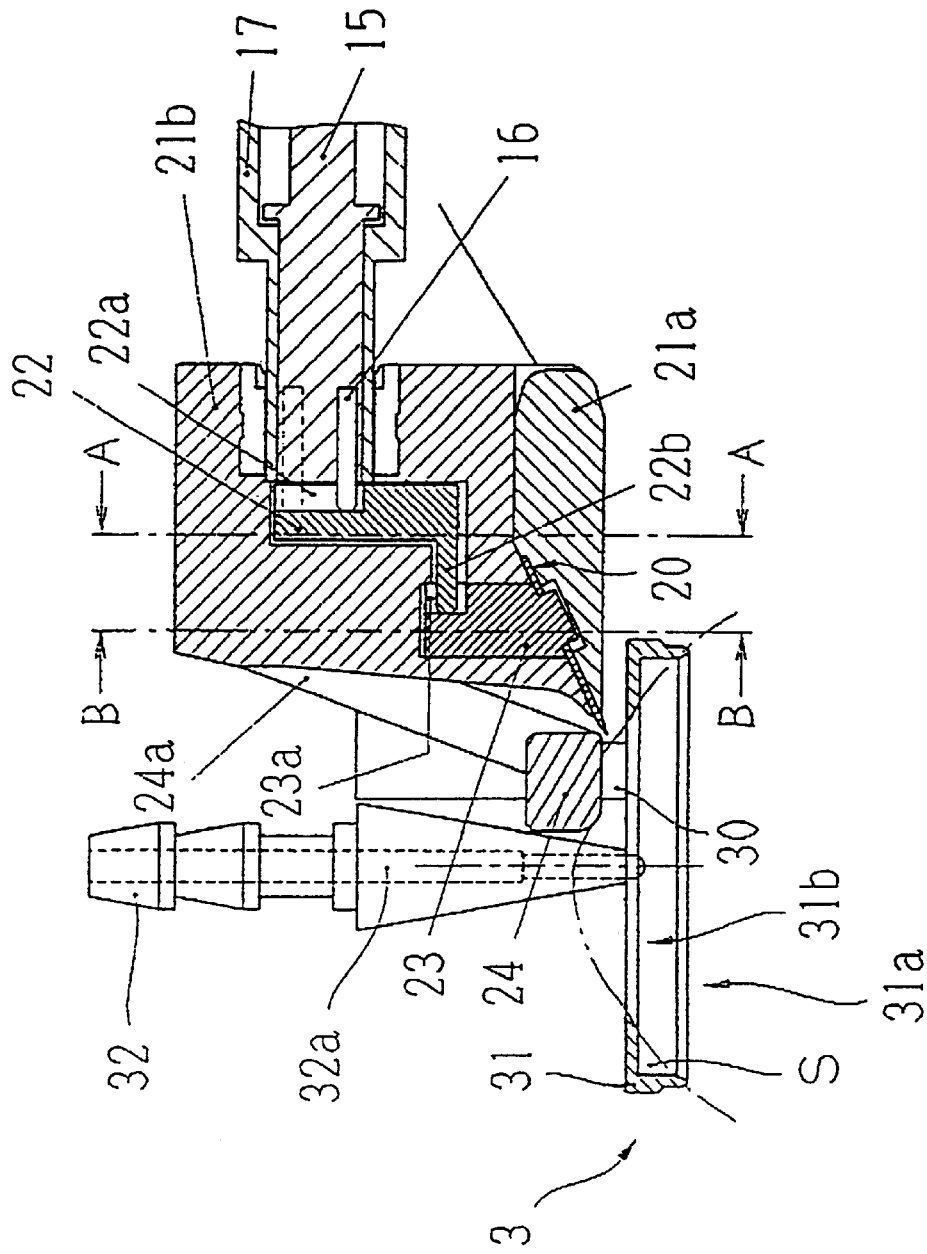
FIG. 2 is an enlarged explanatory diagram of a-cutting unit and a suction unit of the apparatus according to the first embodiment.
Figure 3:
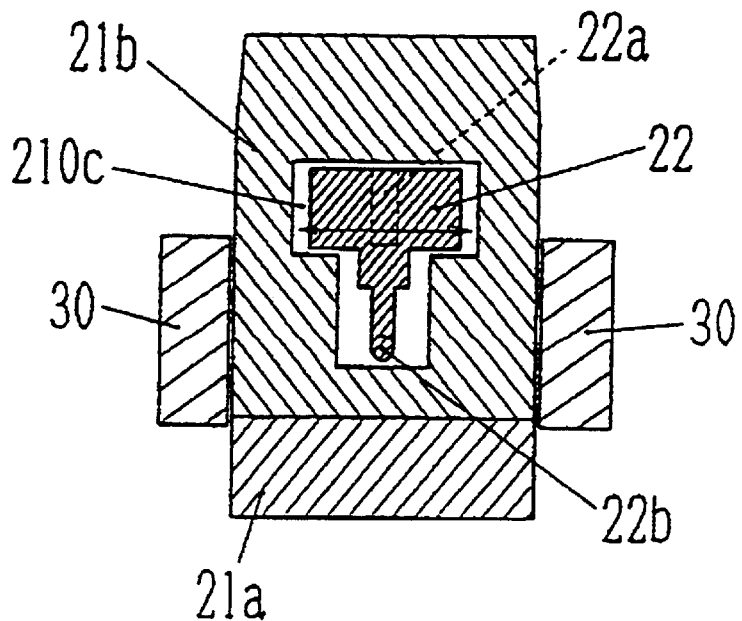
FIG. 3 is a cross-sectional view taken on the line I—I of FIG. 2, illustrating the cutting unit of the apparatus according to the first embodiment.
Figure 4:
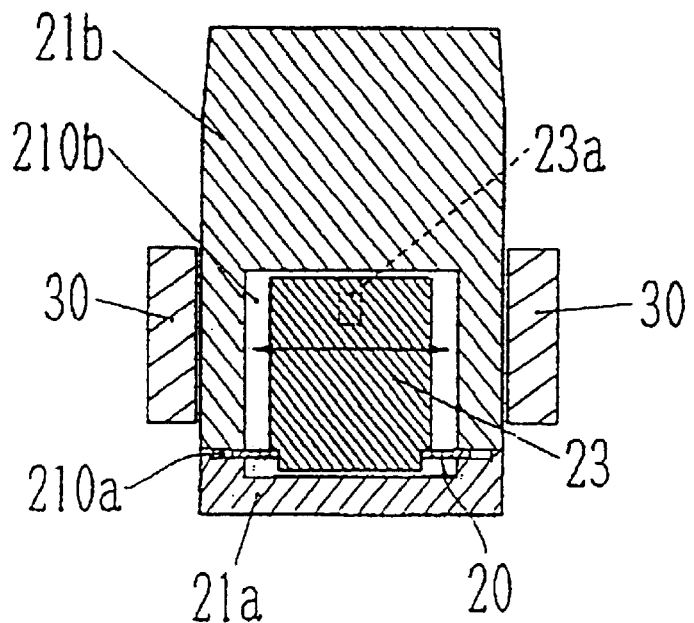
FIG. 4 is a cross-sectional view taken on the line II—II of FIG. 2, illustrating the cutting unit of the apparatus according to the first embodiment.

Next, the configuration of the cutting unit 2 and the suction unit 3 will be explained with reference to FIGS. 2, 3 and 4. FIG. 2 is an enlarged explanatory diagram of the cutting unit 2 and the suction unit 3 of the apparatus according to the first embodiment. FIG. 3 is a cross-sectional view taken on the line I—I of FIG. 2, and FIG. 4 is a cross-sectional view taken on the line II—II of FIG. 2.

The cutting unit 2 comprises the blade 20, a blade holder 21a, a holder block 21b, a first oscillation transmitting member 22, and a second oscillation transmitting member 23. A rotation hole in which the shaft 15 is inserted is provided in the holder block 21b so that the tip portion of the connecting member 17 is fixed thereto.

A metal blade having a blade edge of stainless steel, or steel, or an ore blade having a blade edge of diamond or sapphire is used as the blade 20. The blade 20 is held between the blade holder 21a and the holder block 21b laterally oscillatably with an appropriate angle with respect to the horizontal plane. A shallow recess 210a is formed at a portion, where the blade 20 is to be placed, at the blade holder 21a side. The lateral width of the recess 210a is provided larger than the oscillation width of the lateral oscillation of the blade 20.

The first transmitting member 22 is held laterally movably in an oscillating space 210c formed in the holder block 21b. Further, a vertical groove 22a to be engaged with the pin 16 is formed in the first transmitting member 22. When the shaft 15 is rotated by the rotation drive of the motor 12, a lateral force is applied to the first transmitting member 22 according to the circumferential movement of the pin 16 engaged with the vertical groove 22a. Accordingly, the first transmitting member 22 oscillates laterally.

The second transmitting member 23 is held laterally movably in an oscillating space 210b formed in the holder block 21b. Further, a vertical groove 23a to be engaged with a pin part 22b provided below the first transmitting member 22 is formed in the second transmitting member 23. When the first transmitting member 22 is oscillated laterally by the rotation of the shaft 15 (circumferential movement of the pin 16), the lateral oscillation provides a lateral force to the second transmitting member 23 via the pin part 22b and the vertical groove 23a. Accordingly, the second transmitting member 23 oscillates laterally, and further, the blade 20 fixed to the second transmitting member 23 oscillates laterally as well.

The movement of the first transmitting member 22, the second transmitting member 23, and the blade 20 will be explained with reference to FIGS. 5A and 5B.

Figure 5A:
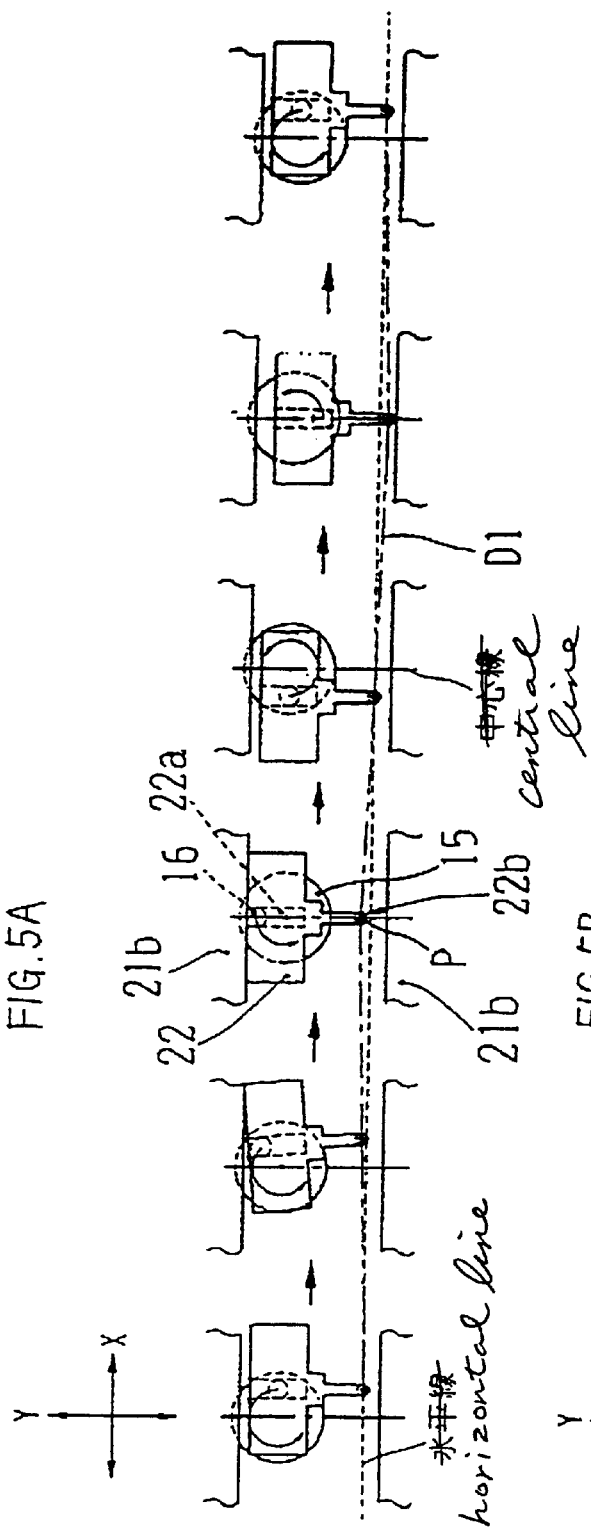
FIGS. 5A and 5B are explanatory diagrams for the movement of two oscillation transmitting members and a blade in the apparatus according to the first embodiment.

The first transmitting member 22 moves reciprocally in the lateral direction (X direction) (this will be referred to as a first lateral oscillation) as well as moves reciprocally in the vertical direction (Y direction) (this will be referred to as a first vertical oscillation) according to the circumferential movement of the pin 16 according to the rotation of the shaft 15 (according to split of the force generated by the circumferential movement of the pin 16 into the pushing force for pushing the side surface of the vertical groove 22a and the friction force functioning in the vertical direction on the side surface of the vertical groove 22a) as shown in FIG. 5A. The dashed line D1 in the figure denotes the locus of the movement of the point P, which is the center of the pin part 22b.

Figure 5B:
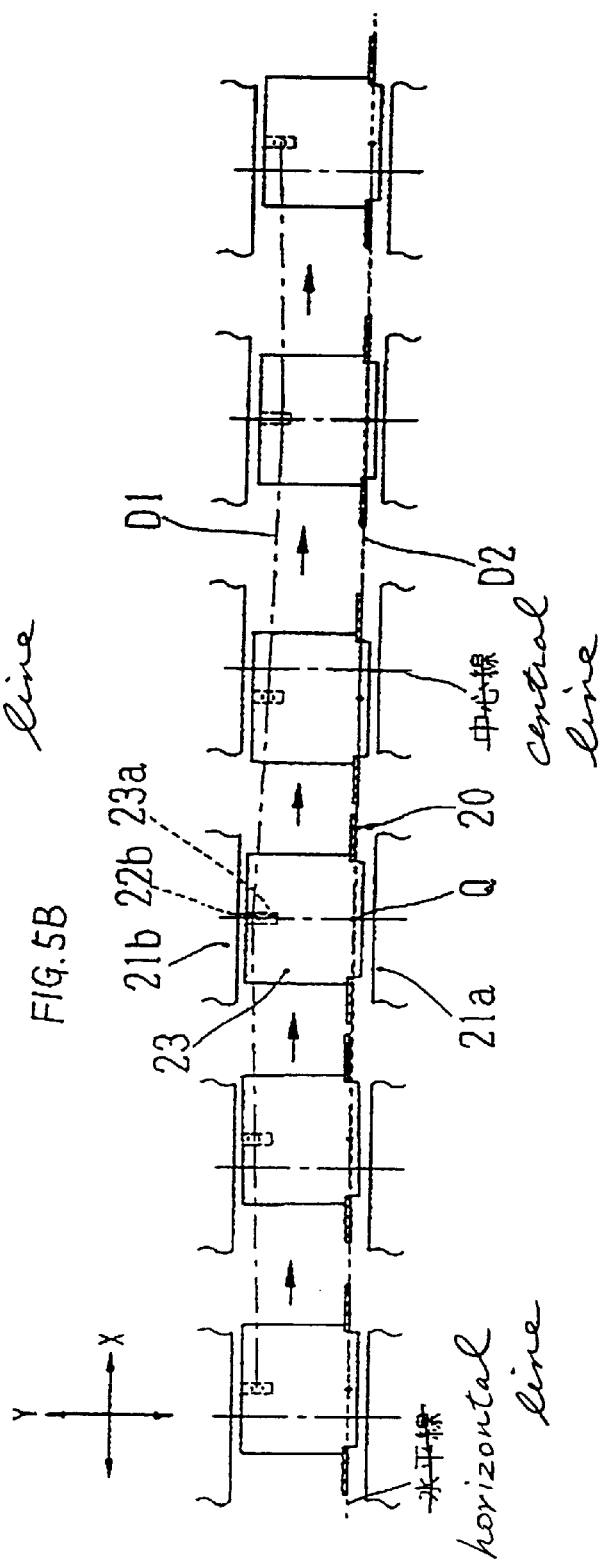

The second transmitting member 23 moves reciprocally in the lateral direction (X direction) (this will be referred to as a second lateral oscillation) as well as slightly moves reciprocally in the vertical direction (Y direction) (this will be referred to as a second vertical oscillation) according to the movement of the pin part 22b of the first transmitting member 22 as shown in FIG. 5B. The dashed line D2 in the figure denotes the locus of the movement of the point Q, which is the center of the blade 20.

The displacement amount in the lateral direction according to the first vertical oscillation is based on the distance of the gap between the first transmitting member 22 and the holder block 21b. In contrast, the displacement amount in the vertical direction according to the second vertical oscillation is much smaller than that of the first vertical oscillation because the circumferential movement of the pin 16 is converted to the first lateral oscillation already, thereby generating the second lateral oscillation (the displacement amount in the lateral direction of the first lateral oscillation and the second lateral oscillation is same, and it corresponds to the eccentric amount of the pin 16). Moreover, the displacement amount difference in the vertical direction according to the second vertical oscillation derived from the gap at the time of generating the first lateral oscillation and the gap at the time of generating the second vertical oscillation is small because the displacement amount itself is extremely small.

As mentioned above, the locus D2 has a smaller displacement amount in the vertical direction compared with the locus D1. That is, the second transmitting member 23 has a smaller displacement amount in the vertical oscillation at the time of the lateral oscillation with respect to the first transmitting member 22. Accordingly, the "rampage" can be restrained at the time of the lateral oscillation.

Figure 6:
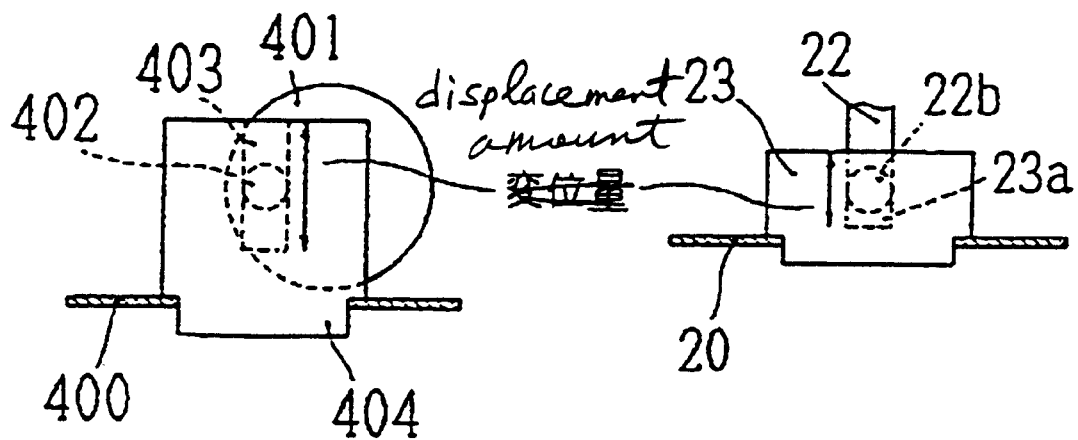
FIG. 6 is an explanatory diagram for the difference of the blade positions in the conventional apparatus and the apparatus according to the first embodiment.
Figure 7:
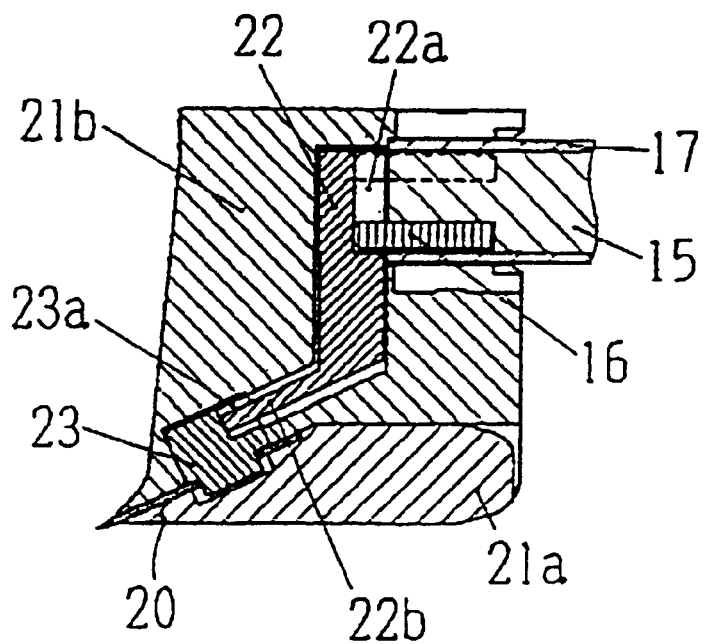
FIG. 7 is a diagram of a modified embodiment of the cutting unit of the apparatus according to the first embodiment.

Furthermore, as shown in FIG. 6, according to the conventional apparatus configuration, the position of a blade 400 in the up and down direction is limited due to the radius (diameter) of a rotation shaft 401, the circumferential movement of an eccentric pin 402, and the displacement amount in the vertical direction (vertical groove 403). In contrast, according to an apparatus of the invention, since the position of the blade 20 in the up and down direction is limited onto to the displacement amount in the vertical direction (vertical groove 23a), and further, the displacement amount in the vertical direction is smaller than the conventional configuration, the point of action for transmitting the lateral oscillation to the second transmitting member 23 can be provided adjacent to the blade 20, to which the load is applied. Therefore, the second transmitting member 23 can be made smaller than the conventional transmitting member 404 (see FIG. 7). Accordingly, the rotation torque applied on the blade 20 is smaller than the conventional configuration, and thus the blade 20 can efficiently be oscillated laterally so that the "rampage" can be smaller.

In FIG. 2, a cornea applanating part 24 is fixed to the holder block 21b by an attaching member 24a so as to be provided on the front side (left side in the figure) of the blade 20. The cornea applanating part 24 moves according to the movement of the cutting unit 2 for applanating the cornea of the patient's eye flatly preceding incision with the blade 20. Since the blade 20 incises the cornea thus applanated flatly by the applanating part 24, a flap of a uniform layer is formed. The distance between the edge of the blade 20 attached to the blade holder 21a and the lower surface of the applanating part 24 is about 150 $\mu$m so that the cornea can be incised with this thickness in a layered form.

The suction unit 3 comprises a fixing member 30, a suction ring 31, and a suction pipe 32. The suction ring 31 is fixed to the main body by the fixing member 30. The suction ring 31 having a substantially cylindrical shape with a U-shaped cross-section, comprises a circular recess 31a to be contacted with the patient's eye and an opening 31b concentric with the recess 31a. When the suction ring 31 is set on the patient's eye for surgery, the cornea of the patient's eye projects upward from the opening 31b so that the lower end portion of the suction ring 31 and the opening end portion of the opening 31b are contacted so as to provide a space S for suction.

The suction pipe 32 is embedded in the suction ring 31, and connected with a vacuum tube (not illustrated) elongating to a pump 41. A suction path 32a provided inside the suction pipe 32 communicates with the recess 31a. According to suction and discharge of the air in the space S by the pump 41 via the suction path 32a, the suction ring 31 is vacuum-fixed to the patient's eye. In this fixation, as the operator holds the grip portion 1a, positioning of the opening 31b can be facilitated, and the apparatus can be held stably.

In addition, a pipe for pressure detection (not illustrated) is embedded in the suction ring 31 at a position facing to the suction pipe 32. The pipe for pressure detection is connected with a pressure detector 33 via a tube (not illustrated). The pressure detector 33 detects the air pressure in the space S sucked by the pump 41 via the pipe for pressure detection. A control unit 40 controls the operation of the motor 11, the motor 12, and the pump 41 based on the air pressure detected by the pressure detector 33.

Hereinafter the operation of the apparatus with the above-mentioned configuration will be described. While confirming the state of inclination of the suction ring 31 (main body 1) and the position of the pupillary center based on a mark applied on the cornea of the patient's eye with an instrument such as a marker, the operator positions the center of the opening 31b with respect to the pupillary center and disposes the suction ring 31 on the patient's eye.

After installation of the suction ring 31, the operator operates the pump 41 so as to suck the air in the space S between the suction ring 31 and the patient's eye while keeping the position and the posture of the main body 1 for thereby reducing the air pressure (to the negative pressure). When the air pressure in the space S is reduced to a certain value (when it reaches a sufficiently negative pressure), the operation of the pump 41 is controlled by the control unit 40 so as to maintain the air pressure. Accordingly, the suction ring 31 is vacuum-fixed onto the patient's eye.

After completion of the fixation of the apparatus, the operator operates a foot switch 42 for rotation drive of the motor 11 and the motor 12. The control unit 40 controls for rotation drive of the motor 11 and the motor 12. The control unit 40 controls the drive of the motor 12 by the input of a drive command signal by the foot switch 42 so as to oscillate the blade 20 laterally by a fixed or variable oscillation frequency. Further, the control unit 40 controls the rotation of the motor 11 according to a fixed or variable feeding speed so as to rectilinearly move the cutting section 2 in the hinge direction. At the time, the shaft 15 slides in the advancing direction integrally with the cutting unit 2 while making a rotational motion for imparting lateral oscillation to the blade 20.

After being converted to the lateral oscillation of the first transmitting member 22, the rotational motion of the shaft 15 is converted to the lateral oscillation of the second transmitting member so as to provide the rectilinear oscillation to the blade 20, and thus the "rampage" caused by the vertical oscillation can be restrained so as to form a good flap stably.

When the edge of the blade 20 has incised the cornea with the hinge portion left so as to complete the flap formation, the motor 11 is rotated reversely so as to return the cutting unit 2 to its initial position. At the time, the rotation of the motor 12 is stopped according to the independent control of the motors so that the blade 20 can be taken out from the flap while avoiding the unnecessary oscillation of the blade 20. Accordingly, the possibility of cut off of the thus formed flap can be reduced.

After the return of the cutting unit 2 to the initial position, air is introduced into the space S so as to release the suction for removing the apparatus (suction ring 31). Subsequently, the corneal stroma is ablated for the refractive correction amount, and then the flap is returned to its original position so as to finish the surgery.

Although the first transmitting member 22 comprising the vertical groove 22a to be engaged with the pin 16 and the pin part 22b, and the second transmitting member 23 comprising the vertical groove 23a to be engaged with the pin part 22b of the first transmitting member 22 (in this case, the blade 20 is fixed to the second transmitting member 23) are used in this embodiment for converting the rotation of the shaft 15 (circumferential movement of the pin 16) to the lateral oscillation of the blade 20, it is also possible to further provide a pin part similar to the pin part 22b in the second transmitting member and a third oscillation transmitting member comprising a vertical groove to be engaged with the pin part of the second transmitting member. In this case, the blade is fixed to the third transmitting member. That is, although the rotation of the rotation shaft is converted to the lateral oscillation of the blade by the conversion by twice, but the conversion needs to be at least twice and can be increased to three times or four times.

Second Embodiment

Figure 8:
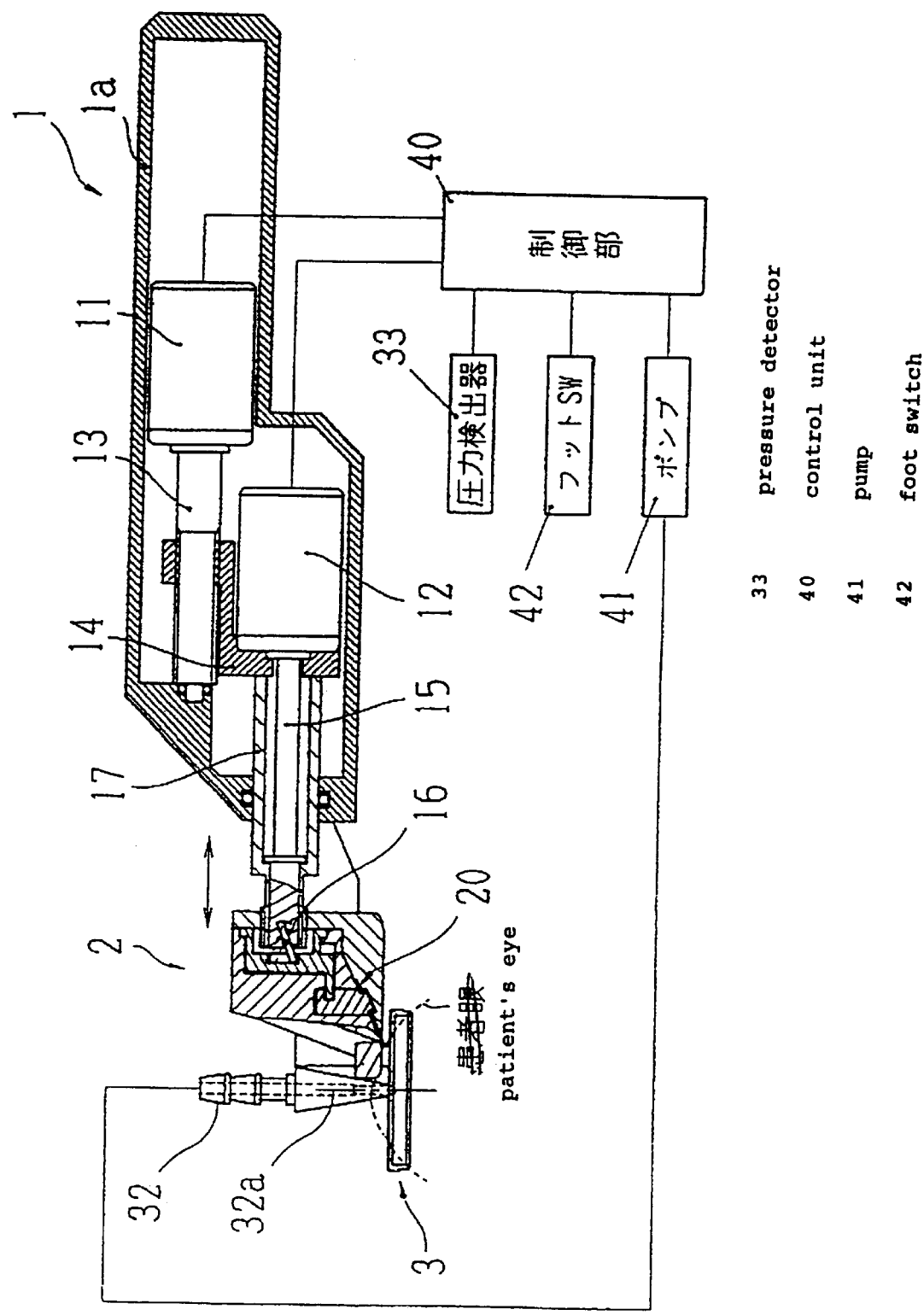
FIG. 8 is a cross-sectional view of an apparatus according to a second embodiment and a schematic diagram of a control system.
Figure 9:
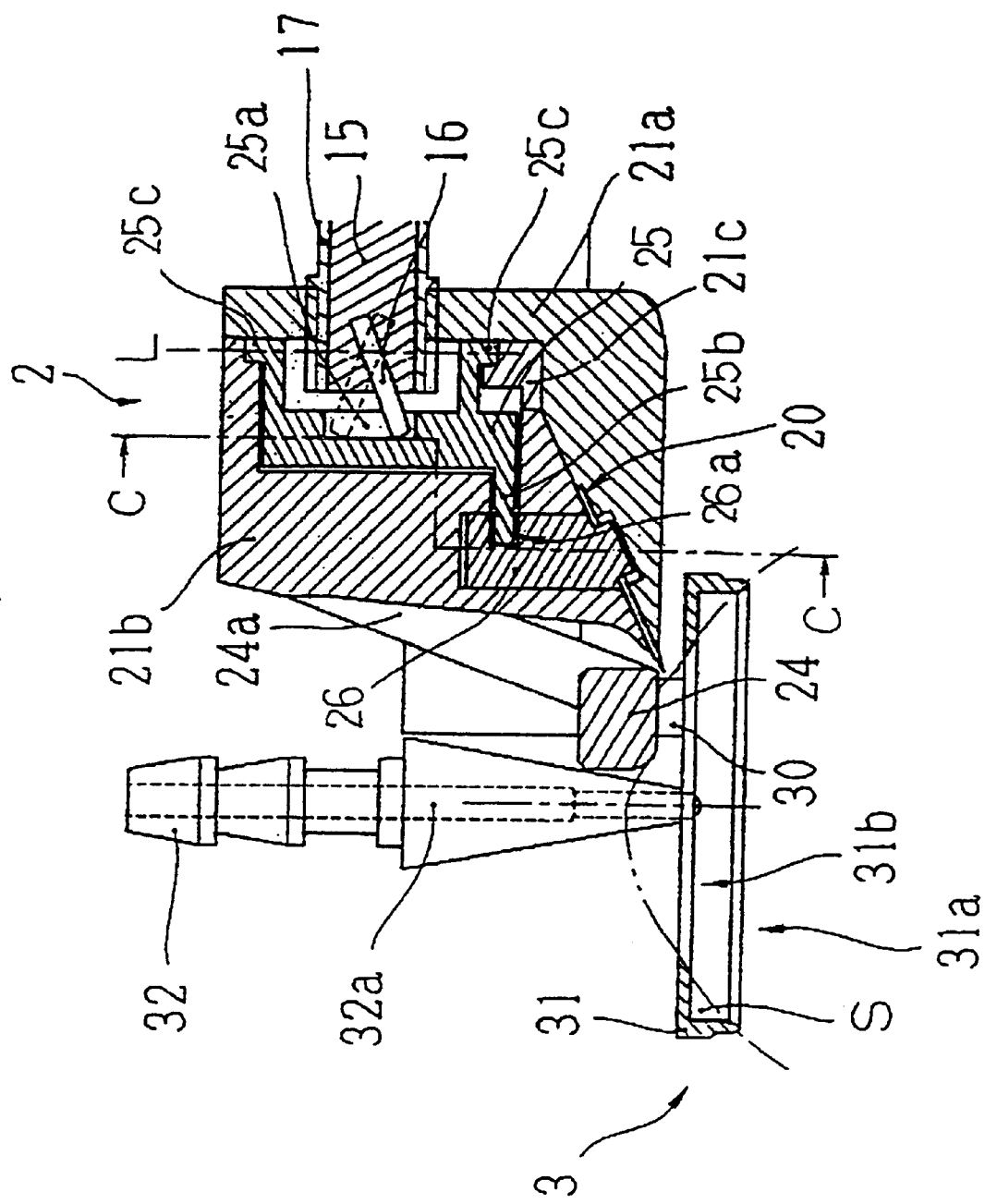
FIG. 9 is an enlarged explanatory diagram of a cutting unit and a suction unit of the apparatus according to the second embodiment.
Figure 10:
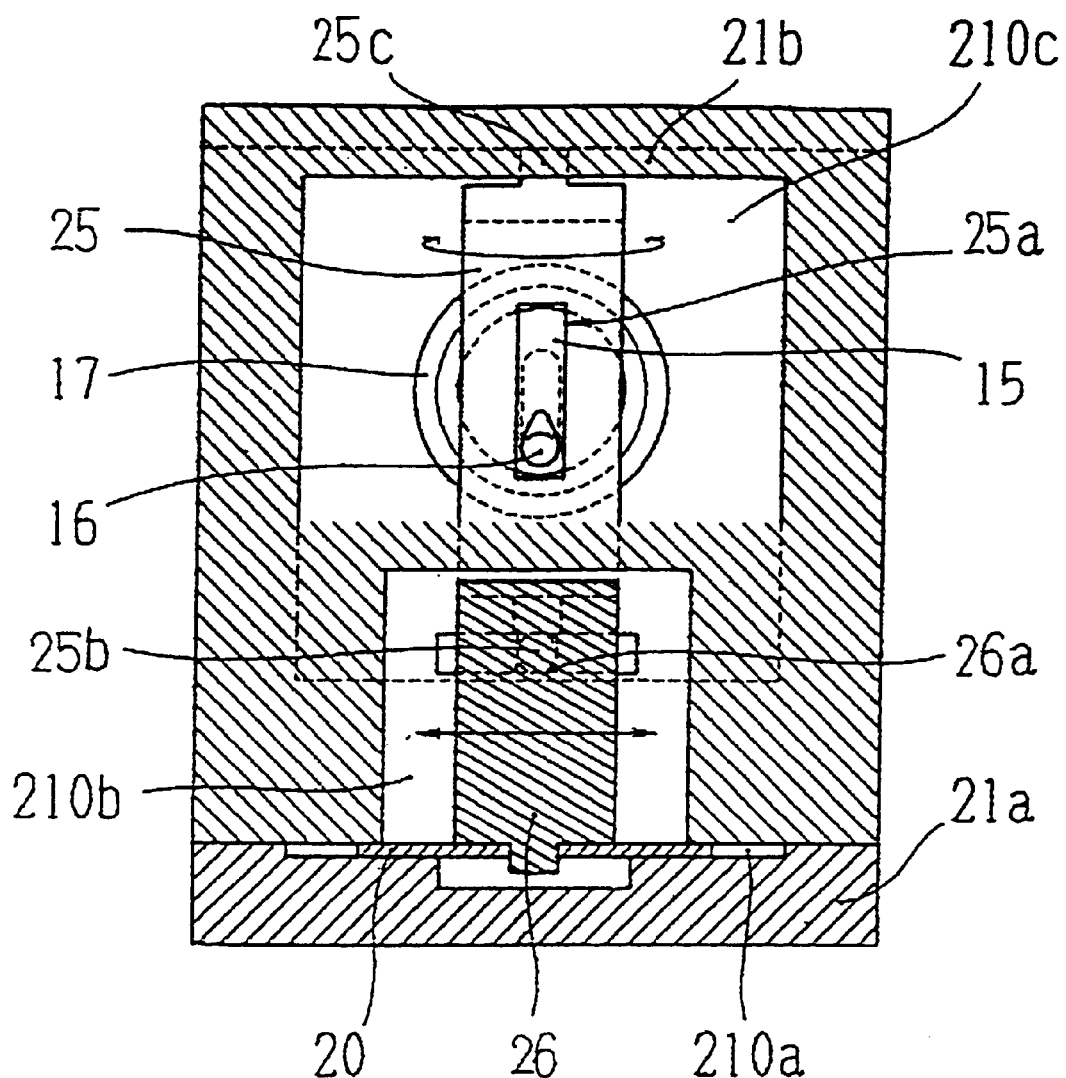
FIG. 10 is a cross-sectional view taken on the line III—III of FIG. 9, illustrating the cutting unit of the apparatus according to the second embodiment.

Another embodiment of the invention will be explained with reference to the drawings. FIG. 8 is a cross-sectional view of an apparatus according to the second embodiment and a schematic diagram of a control system. FIG. 9 is an enlarged cross-sectional view of a cutting unit 2 and a suction unit 3. FIG. 10 is a cross-sectional view taken on the line III—III of FIG. 9. The same numerals are applied to the same components as in the first embodiment.

The cutting unit 2 comprises the blade 20, the blade holder 21a, the holder block 21b, a bearing part 21c, a rock (swing) transmitting member 25, and a lateral oscillation transmitting member 26. A rotation hole in which the shaft 15 is inserted is provided in the blade holder 21a so that the tip portion of the connected member 17 is fixed thereto.

The rock transmitting member 25 is pivoted between the holder block 21b and the bearing part 21c rotatably (rockably) with two upper and lower rotation shaft parts 25c as the rotation central axis in the oscillation space 210c formed in the holder block 21b (that is, the rock transmitting member 25 is pivoted rockably in the lateral direction, centering the axial line L elongating in the vertical direction). Further, a vertical groove 25a to be engaged with the pin 16 is formed in the rock transmitting member 25. When the shaft 15 is rotated according to the rotation drive of the motor 12, a force in the lateral direction is applied on the rock transmitting member 25 by the circumferential movement of the pin 16 engaged with the vertical groove 25a. Accordingly the rock transmitting member 25 is rocked.

The lateral oscillation transmitting member 26 is held movably in the lateral direction in the oscillation space 210b formed in the holder block 21b. A pin receiving part 26a to be engaged with the a pin part 25b provided at a lower portion of the rock transmitting member 25 is formed in the lateral oscillation transmitting member 26. When the rock transmitting member 25 is rocked in the lateral direction with the shaft parts 25c as the rotation center by the rotation of the shaft 15 (circumferential movement of the pin 16), a force in the lateral direction is applied on the lateral oscillation transmitting member 26 via the pin part 25b and the pin receiving part 26a according to the rock. Accordingly, the lateral oscillation transmitting member 26 oscillates laterally, and further, the blade 20 fixed to the oscillation transmitting member 26 oscillates laterally as well.

Figure 11:
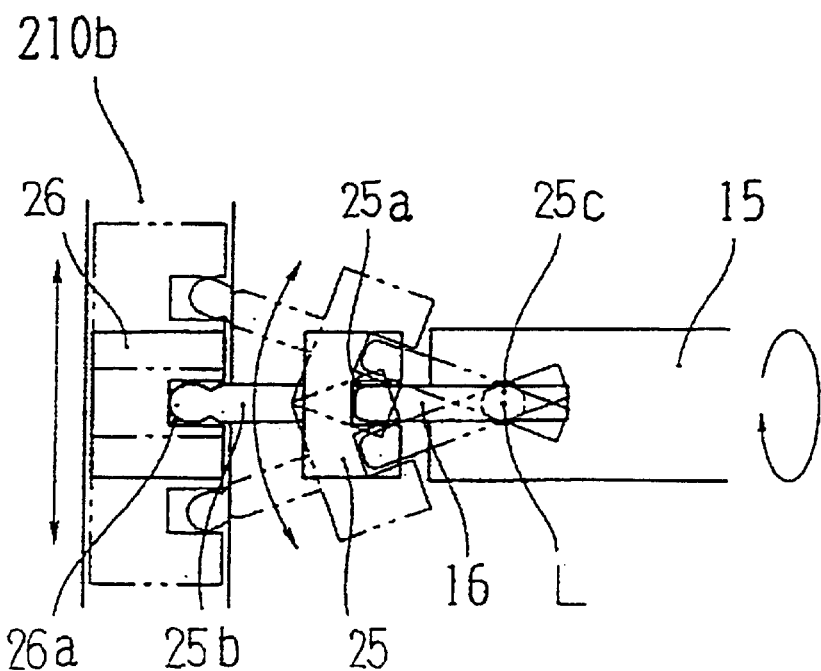
FIG. 11 is an explanatory diagram for conversion of the motion in the apparatus according to the second embodiment.

The movement of the pin 16, the rock transmitting member 25, the lateral oscillation transmitting member 26, and the blade 20 will be explained with reference to FIG. 11.

When the shaft 15 is rotated by the motor 12, the projecting portion of the pin 16 provided eccentrically in the shaft 15 moves circumferentially, centering the rotation central axis of the shaft 15. The force generated by the circumferential movement of the pin 16 can be split in the vertical and lateral directions, that is, the force in the vertical direction functioning on the side surface of the vertical groove 25a in the up and down direction as the friction force, and the force in the lateral direction pushing the side surface of the vertical groove 25a in the lateral direction as the pushing force. According to the force applied on the side surface of the vertical groove 25a, the rock transmitting member 25 rocks with the shaft parts 25c as the rotation center. Since the shaft parts 25c are held sufficiently by the holder block 21b and the bearing part 21c with respect to the force in the vertical direction generated by the pin 16, the "rampage" in the vertical direction an be restrained so that the rotational motion of the shaft 15 can be converted efficiently to the rock of the rock transmitting member 25.

According to the rock of the rock transmitting member 25 in the lateral direction, the pin part 25b formed in the lower portion thereof is rocked in the lateral direction with substantially no displacement in the vertical direction. Since the pin part 25b rocking in the lateral direction applies a force on the side surface of the pin receiving part 26a, the lateral oscillation transmitting member 26 oscillates in the lateral direction with the oscillation space 210b as the guide. At the time, by providing a substantially spherical tip end shape to the pin part 25b, a force can be applied efficiently to the pin receiving part 26a so that the lateral oscillation can be provided smoothly. Since the blade 20 is fixed to the lateral oscillation transmitting member 26, it oscillates according to the lateral oscillation of the lateral oscillation transmitting member 26.

According to the configuration, after being converted to the rock with the shaft parts 25c of the rock transmitting member 25 as the rotation center, the rotational motion of the shaft 15 applies rectilinear oscillation to the blade 20 in the lateral direction. Since the force according to the circumferential movement of the pin 16 in the vertical direction is supported by the shaft parts 25c, the "rampage" by the vertical oscillation can be restrained so that a good flap can be formed stably. Moreover, since the sliding portion is only in the peripheral part of the shaft parts 25c, worn out parts of the oscillating portion can be restrained so as to prolong the life cycle of the parts.

Figure 13A:
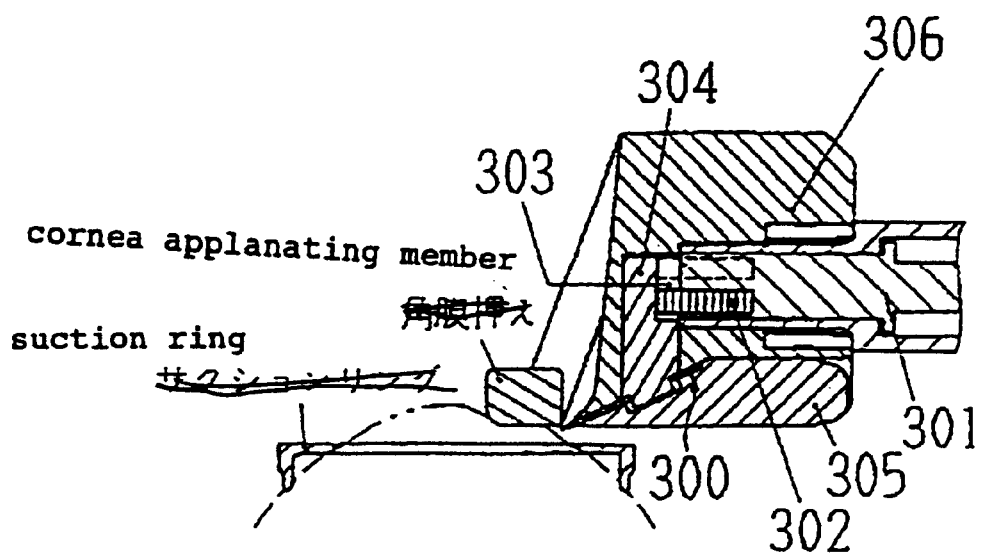
FIGS. 13A and 13B are explanatory diagrams for the configuration of a cutting unit, and the movement of a transmitting member and a blade in a conventional mechanism.
Figure 13B:
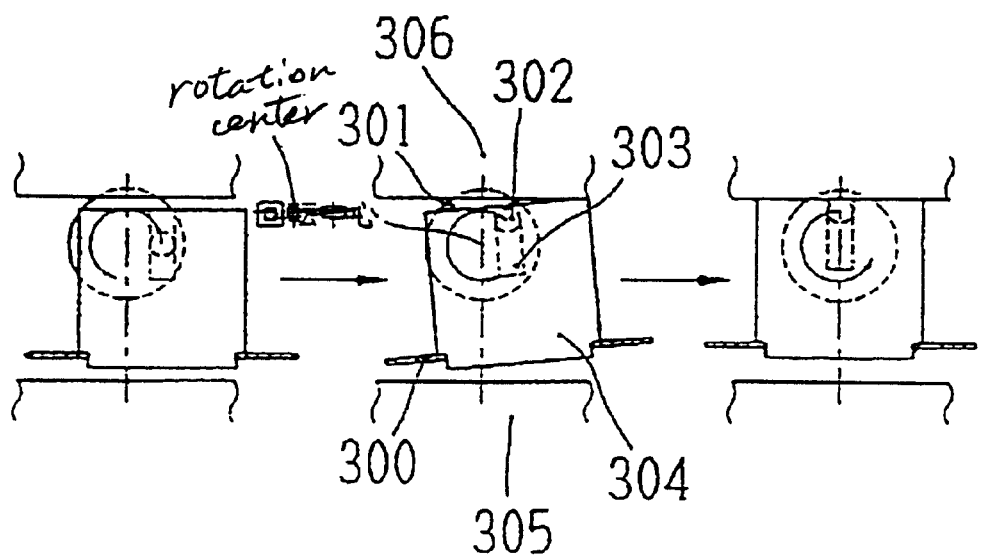

The pin 16 can be attached to the shaft 15, elongating parallel in the rotation central axis direction of the shaft 15 (as in the conventional apparatus shown in FIG. 13A), but the pin 16 is provided tilting with respect to the rotation central axis direction of the shaft 15 in this embodiment. That is, the pin 16 is provided eccentrically passing through the intersection of the axial line L passing through the rotation center of the rock of the rock transmitting member 25 and the rotation central axis of the shaft 15. According to the configuration, since the rocking angle of the pin 16 in the lateral direction and the rocking angle of the rock transmitting member 25 in the lateral direction coincide, the contacting property of the pin 16 engaged with the vertical groove 25a is improved and thus the rotational motion can be converted smoothly and efficiently to the lateral rock. Moreover, the shape of the vertical groove 25a and the tip end portion shape of the pin 16 to be engaged therewith can be a simple shape (linear shape) so that the production of components can be facilitated.

Figure 12:
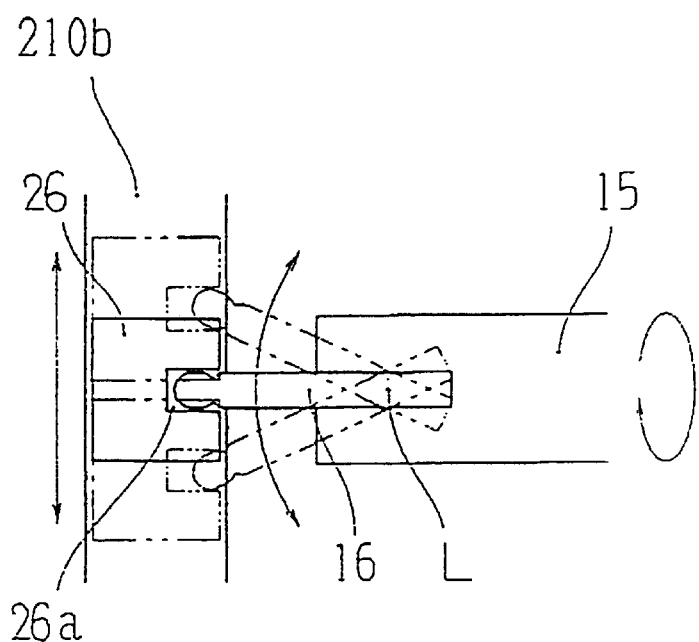
FIG. 12 is a diagram of a modified embodiment of the cutting unit of the apparatus according to the second embodiment.

Furthermore, although the rock of the pin part 25b is converted to the linear lateral oscillation of the lateral oscillation transmitting member 26 in this embodiment, it is also possible to fix the pin part 25b and the lateral oscillation transmitting member 26, rock the lateral oscillation transmitting member 25, and have arc-like oscillation of the blade 20. Moreover, as shown in FIG. 12, the rock transmitting member 25 can be eliminated.

Furthermore, the rock transmitting member 25 needs to rock with oscillation with a lateral direction component for oscillating the blade 20 in the lateral direction, and therefor, the axial line L to be the center of the rock should be provided at a position offset from the rotation central axis of the shaft 15. For the efficient conversion of the rotation of the shaft 15 into the oscillation of the lateral direction component, it is preferable that the axial line L to be the center of the rock is in the same plane as the rotation central axis of the shaft 15, and further, it is preferable that the axial line L as the rocking center is disposed in the plane in the vertical direction passing through the rotation central axis of the shaft 15 with respect to the lateral direction for oscillating the blade 20, and the rock transmitting member 25 is rocked with the axial line L as the center. The conversion efficiency of the oscillation in the lateral direction can be most efficient by providing the axial line L orthogonal to the rotation central axis of the shaft 15 as in this embodiment.

Moreover, the vertical groove 25a formed in the rock transmitting member 25 can be provided at the grip portion la side with respect tot he rotation center of the shaft parts 25c. Furthermore, by changing the distance of the vertical groove 25a and the distance of the pin 25b from the rotation center of the shaft parts 25c, respectively, the width of the lateral oscillation of the blade 20 with respect to the eccentric amount of the pin 16 can be adjusted freely (it is also possible to enlarge the oscillation width with a small eccentric amount).

Moreover, although explanation has been given with the motor 12 for rotating the shaft 15 in this embodiment, an air turbine can be used as well. Furthermore, as the mechanism for feeding the blade, a mechanism for incising the cornea by rotational movement of the blade as disclosed in JP-A-11-19115 and JP-A-11-99167 filed by the present inventor can be adopted as well.

As heretofore explained according to the invention, a good flap can be formed by preventing the "rampage" of the blade.

Moreover, the lateral oscillation of the blade can be generated efficiently, the cost rise according to the high accuracy of the mechanism can be restrained, and the durability of the mechanism is improved so as to prolong the life cycle.

What is claimed is:

1. A corneal surgical apparatus for incising a cornea of a patient's eye in a layered form, comprising:
   a suction ring unit, having a circular opening, that is to be vacuum-fixed onto a peripheral part of the cornea;
   a rotatable shaft;
   an eccentric pin projecting from a distal end of the shaft, the eccentric pin being located at a position offset from a rotational central first axis of the shaft; and
   a cutting unit movable in an incising direction relative to the suction ring unit, the cutting unit including:
      cornea applanating means that applanates the cornea within the opening into a substantially flat form;
      a blade that incises the cornea;
      a rock transmitting member having a part with which the eccentric pin is engaged and a shaft part rockable about a second axis, the shaft part having at least one of a recess and a protrusion; and
      a holder that holds the rock transmitting member to be rockable in a lateral direction which is perpendicular to the rotational central first axis of the shaft, the holder having a bearing part rockably supporting the shaft part of the rock transmitting member, the bearing part having a part with which the shaft part is engaged,
   wherein movement of the rock transmitting member in the lateral direction causes the blade to be moved in the same direction.

2. A corneal surgical apparatus according to 1, wherein the shaft part of the rock transmitting member includes a first shaft portion located on an upper part of the rock transmitting member and a second shaft portion located on a lower part of the rock transmitting member, and
   wherein the bearing part includes a first bearing part and a second bearing part respectively supporting the first and second shaft portions.

3. A corneal surgical apparatus according to 1, wherein the second axis intersects the rotational central first axis of the shaft.

4. A corneal surgical apparatus according to 3, wherein the second axis perpendicularly intersects the rotational central first axis of the shaft.

5. A corneal surgical apparatus according to 4, wherein the eccentric pin is provided on an axis passing through an intersecting point at which the second axis intersects the rotational central first axis of the shaft.

6. A corneal surgical apparatus according to 1, wherein the eccentric pin is provided on an axis which non-perpendicularly intersects the rotational central first axis of the shaft.

7. A corneal surgical apparatus according to claim 1, further comprising:

a drive unit that rotates the shaft.

8. A corneal surgical apparatus according to claim 1, further comprising:

a drive unit that moves the cutting unit in the incising direction.

9. A corneal surgical apparatus for incising a cornea of a patient's eye in a layered form, comprising:

a suction ring unit, having a circular opening, that is to be vacuum-fixed onto a peripheral part of the cornea;

a rotatable shaft;

an eccentric pin projecting from a distal end of the shaft, the eccentric pin being provided on an axis non-parallel to and non-perpendicular to a rotational central axis of the shaft; and a cutting unit movable in an incising direction above the suction ring unit, the cutting unit including:

cornea applanating means that applanates the cornea within the opening into a substantially flat form;

a blade that incises the cornea;

a transmitting member having a part with which the eccentric pin is engaged; and a holder that holds the transmitting member to be movable in a lateral direction which is perpendicular to the rotational central axis of the shaft, wherein movement of the transmitting member in the lateral direction causes the blade to be moved in the same direction.

10. A corneal surgical apparatus according to claim 9, wherein the eccentric pin is provided on an axis that non-perpendicularly intersects the rotational central axis of the shaft.

11. A corneal surgical apparatus according to claim 9, further comprising:

a drive unit that rotates the shaft.

12. A corneal surgical apparatus according to claim 9, further comprising:

a drive unit that moves the cutting unit in the incising direction.

* * * * *

UNITED STATES PATENT AND TRADEMARK OFFICE
CERTIFICATE OF CORRECTION

PATENT NO. : 6,344,046 B2
DATED : February 5, 2002
INVENTOR(S) : Masahiro Sugimura et al.

It is certified that error appears in the above-identified patent and that said Letters Patent is hereby corrected as shown below:

Column 13,
Line 24, "direction above the" should read -- direction relative to the --.

Signed and Sealed this

First Day of April, 2003

JAMES E. ROGAN
*Director of the United States Patent and Trademark Office*